(12) United States Patent
    Yun et al.

(10) Patent No.: US 11,179,423 B2
(45) Date of Patent: Nov. 23, 2021

(54) METHODS OF ENHANCING FEMALE FERTILITY

(71) Applicant: Palo Alto Investors, Palo Alto, CA (US)

(72) Inventors: Anthony Joonkyoo Yun, Menlo Park, CA (US); Conrad Minkyoo Yun, San Mateo, CA (US); Kimberly A. Bazar, Palo Alto, CA (US)

(73) Assignee: Palo Alto Investors, Palo Alto, CA (US)

( * ) Notice: Subject to any disclaimer, the term of this patent is extended or adjusted under 35 U.S.C. 154(b) by 312 days.

(21) Appl. No.: 15/976,413

(22) Filed: May 10, 2018

(65) Prior Publication Data

US 2018/0344778 A1    Dec. 6, 2018

Related U.S. Application Data

(60) Provisional application No. 62/513,288, filed on May 31, 2017.

(51) Int. Cl.
    *A61K 35/54*    (2015.01)
    *C12N 15/877*    (2010.01)
    *C12N 5/0735*    (2010.01)
    *C12N 5/075*    (2010.01)

(52) U.S. Cl.
    CPC ............ *A61K 35/54* (2013.01); *C12N 5/0606* (2013.01); *C12N 5/0609* (2013.01); *C12N 15/8776* (2013.01); *C12N 2500/02* (2013.01); *C12N 2501/125* (2013.01); *C12N 2501/602* (2013.01); *C12N 2501/603* (2013.01); *C12N 2501/604* (2013.01); *C12N 2501/606* (2013.01); *C12N 2501/70* (2013.01); *C12N 2513/00* (2013.01); *C12N 2517/10* (2013.01)

(58) Field of Classification Search
    CPC .... A61K 35/43; C12N 5/0606; C12N 5/0609; C12N 15/8776; C12N 2500/02; C12N 2501/125; C12N 2501/602; C12N 2501/603; C12N 2501/604; C12N 2501/606; C12N 2501/70; C12N 2513/00; C12N 2517/10
    See application file for complete search history.

(56) References Cited

U.S. PATENT DOCUMENTS

2010/0221827 A1*  9/2010  Jaenisch ..................... 435/354
2012/0087898 A1*  4/2012  Tilly ........................... 424/93.7
2016/0024527 A1*  1/2016  Tilly

OTHER PUBLICATIONS

Ocampo et al., "In Vivo Amelioration of Age-Associated Hallmarks by Partial Reprogramming", Dec. 15, 2016, Cell 167, p. 1719-1733.*
Zou et al., "Production of offspring from a germline stem cell line derived from neonatal ovaries", 2009, Nature Cell Biology 11(5), p. 631-636.*
Anchan et al., "Efficient Differentiation of Steroidogenic and Germ-Like Cells from Epigenetically-Related iPSCs Derived from Ovarian Granulosa Cells", 2015, Public Library of Science ONE 10(3), p. 1-21.*
Sigma Aldrich, "Millicell Hanging Cell Culture Inserts Single and Preloaded Inserts", 2009, Electronic Resource [http://101.200.202.226/files/prod/manuals/201604/08/582157001.pdf], accessed on Jun. 2, 2020.*
Pereira et al., "Reprogramming cell fates: insights from combinatorial approaches", 2012, Annals of the New York Academy of Sciences 1266, p. 7-17.*
Awe et al, "Identifying Candidate Oocyte Reprogramming Factors Using Cross-Species Global Transcriptional Analysis", 2013 Cellular Reprogramming 15(2), p. 126-133.*
Hanna et al., "Ovarian germline stem cells: an unlimited source of oocytes?", 2014, Fertility and Sterility 101(1), p. 20-30.*
White et al., "Oocyte formation by mitotically active germ cells purified from ovaries of reproductive-age women", 2012, Nature Medicine 18(3), p. 414-421.*
Woods et al, "Purification of Oogonial Stem Cells From Adult Mouse and Human Ovaries: An Assessment of the Literature and a View Toward the Future", 2013, Reproductive Sciences 20(1), p. 7-15.*
Parvari et al., "Differentiation of Mouse Ovarian Stem Cells Toward Oocyte-Like Structure by Coculture with Granulosa Cells", Nov. 2016, Cellular Reprogramming 18(6), p. 419-428.*
Merdan et al., "Pegylated Polyethylenimine-Fab' Antibody Fragment Conjugates for Targeted Gene Delivery to Human Ovarian Carcinoma Cells", 2003, Bioconjugate Chem. 14, p. 989-966.*
Mahasreshti et al., "Ovarian cancer targeted adenoviral-mediated mda-7/IL-24 gene therapy", 2006, Gynecologic Oncology 100, p. 521-532.*
Abad et al., "Reprogrammingi n vivo produces teratomas and iPS cells with totipotency features", 2013, Nature 502, p. 340-345.*
Brazdova et al., Immune Aspects of Female Infertility, Royan Institute International Journal of Fertility and Sterility vol. 10, No. 1, Apr.-Jun. 2016, pp. 1-10.
Bukovsky et al., Origin of germ cells and formation of new primary follicles in adult human ovaries, Reproductive Biology and Endocrinology 2004, 2:20.
Carey et al., Single-gene transgenic mouse strains for reprogramming adult somatic cells, Nat Methods. Jan. 2010; 7(1): 56-59.
David et al., Uptake of tritiated thymidine by primordial germinal cells in the ovaries of the adult slender loris, J Reprod Fertil. Dec. 1974;41(2):447-51.
Fereydouni et al., The neonatal marmoset monkey ovary is very primitive exhibiting many oogonia, Reproduction. Aug. 2014;148(2):237-47.
Hanna et al., Ovarian germline stem cells: an unlimited source of oocytes?, Fertil Steril. Jan. 2014;101(1):20-30.

(Continued)

*Primary Examiner* — Robert M Kelly
(74) *Attorney, Agent, or Firm* — Peter W. Schroen; Bret E. Field; Bozicevic, Field & Francis LLP

(57) ABSTRACT

Methods of enhancing fertility of a female subject by increasing the number of oogonia present in the ovary of the female subject are provided. Aspects of the methods include methods of in vivo expansion of oogonia as well as methods of ex vivo expansion of oogonia.

13 Claims, No Drawings

(56) References Cited

OTHER PUBLICATIONS

Izzo et al., Human reproduction: current status, Rev Assoc Med Bras (1992). Nov.-Dec. 2015;61(6):557-9.

Li et al., 3D Culture Supports Long-Term Expansion of Mouse and Human Nephrogenic Progenitors, Cell Stem Cell. Oct. 6, 2016;19(4):516-529.

Ocampo et al., In Vivo Amelioration of Age-Associated Hallmarks by Partial Reprogramming, Cell. Dec. 15, 2016; 167(7):1719-1733.

Silvestris et al., Perspective in infertility: the ovarian stem cells, Journal of Ovarian Research (2015) 8:55.

Szotek et al., Normal ovarian surface epithelial label-retaining cells exhibit stem/progenitor cell characteristics, Proc Natl Acad Sci U S A. Aug. 26, 2008; 105(34):12469-73.

Virant-Klun et al., Parthenogenetic Embryo-Like Structures in the Human Ovarian Surface Epithelium Cell Culture in Postmenopausal Women with No Naturally Present Follicles and Oocytes, Stem Cells Dev. Jan.-Feb. 2009;18(1)137-49.

Woods et al., Purification of Oogonial Stem Cells From Adult Mouse and Human Ovaries: An Assessment of the Literature and a View Toward the Future, Reprod Sci. Jan. 2013;20(1):7-15.

Wu et al., An alternative pluripotent state confers interspecies chimaeric competency, Nature. May 21, 2015; 521(7552): 316-321.

Yang et al., Derivation of Pluripotent Stem Cells with in Vivo Embryonic and Extraembryonic Potency, Cell. Apr. 6, 2017;169(2):243-257.

Black et al., Reproductive, Maternal, Newborn, and Child Health, Disease Control Priorities, Third Edition, vol. 2, World Bank Group, Washington, 2016.

White et al., Oocyte formation by mitotically-active germ cells purified from ovaries of reproductive age women, Nat Med., Sep. 2012, 18(3)413-421.

Yazdekhasti et al., Used protocols for isolation and propagation of ovarian stem cells, different cells with different traits, J Ovarian Res., Oct. 2016; 9:68.

Maurice et al., Efficient Gene Delivery to Quiescent Interleukin-2 (IL-2)-Dependent Cells by Murine Leukemia Virus-Derived Vectors Harboring IL-2 Chimeric Envelopes Glycoproteins, Blood, vol. 94, No. 2 (Jul. 15), 1999: pp. 401-410.

\* cited by examiner

METHODS OF ENHANCING FEMALE FERTILITY

CROSS-REFERENCE TO RELATED APPLICATIONS

Pursuant to 35 U.S.C. § 119 (e), this application claims priority to the filing date of United States Provisional Patent Application Ser. No. 62/513,288 filed May 31, 2017; the disclosure of which application is herein incorporated by reference.

INTRODUCTION

In 2010, an estimated 48.5 million couples worldwide were unable to have a child after five years of trying (See Mascarenhas et al., PLoS Med. 2012; 9(12):e1001356). Global infertility prevalence rates are difficult to determine, due to the presence of both male and female factors which complicate making any estimate which specifically addressed the female contribution to a couple's infertility. However, studies have shown that more women in developed countries, the United States included, are waiting until later in life to start having children. In 2013, the U.S. saw a record high average age of 26 years old for women having their first child, an increase of 3.3 years since 1980 (Marin et al., *National Vital Statistics Report*. (2015) 64(1):1-66). The average age of first-time mothers is increasing because more women are waiting until their 30s and 40s to start having kids and fewer women are having their first children in their teens and 20s. Fertility treatments have facilitated this trend making it easier in some cases, and possible in others, for women to have children later in life.

Roughly 1.3 million patients receive infertility advice or treatment each year in the U.S. The emotional effects of infertility, whether a result of a medical condition preventing pregnancy or decreased fertility due to advanced age, negatively impact many relationships and marriages. One study of 200 couples seen consecutively at a fertility clinic, for example, found that half of the women and 15% of the men said that infertility was the most upsetting experience of their lives (see *Harvard Mental Health Letter*, May 2009). In addition, advanced infertility treatments are expensive. The average cost of in vitro fertilization treatment in the U.S. is currently about $11,000 to $12,000 and even less aggressive treatments such as intrauterine insemination and ovarian stimulation can cost many hundreds to a few thousand dollars. There are no indications that rates of infertility are dropping or that this trend, increasing average age of first pregnancy, will reverse.

In sexually reproducing organisms, oogonia are derived from primordia germ cells following migration of the primordial germ cells into the ovary. During development oogonia initiate meiosis, and often pause after initiation, to form reproductively competent oocytes. Many organisms maintain oogonia well into adulthood, including e.g., *Drosophila, C. elegans, Oryzias latipes* and *Danio rerio* (see Hana et al., Fertil Steril (2014) 101:20-30) and it appears that the presence of self-renewing germ cell compartments may be the exception rather than the rule (see Spradling et al. Cold Spring Harb Prespect Biol. (2011) 3:a002642). Mitotic germinal cells have been detected in neonate and adult primates (see e.g., David et al. (J. Reprod. Fert. (1974) 41:447-451) and Fereydouni et al. (Reproduction (2014) 148 237-247)). In addition, the existence of postnatal oogenesis in mammals is supported by the isolation and propagation of ovarian stem cells from adult mice and humans that have been differentiated into productive oocytes (see e.g., Woods et al. (Reproductive Sciences (2013) 20(1):7-15) and White et al. (Nat Med. (2012) 18(3):413-421)).

SUMMARY

Methods of enhancing fertility of a female subject by increasing the number of oogonia present in the ovary of the female subject are provided. Aspects of the methods include methods of in vivo expansion of oogonia as well as methods of ex vivo expansion of oogonia.

Definitions

The term "fertility", as used herein, generally refers to the capacity to conceive or to induce conception of offspring. Accordingly, "infertility" generally refers to the inability to conceive or to induce conception of offspring. Infertility may be determined based on a duration of time, during which a mating couple or sexual partners having intercourse without contraception are unable to conceive offspring. In some instances, infertility may be indicated after a duration of about one year without conception. Female fertility may refer to the ability of a female to produce productive eggs or ova and/or the ability of a female to ovulate, i.e., discharge ova from the ovary. In some instances, infertility may be a result of menopause.

The term "menopause", as used herein, generally refers to the end of menstruation of a female subject. Menopause includes a decline in estrogen resulting in a wide range of changes in various tissues that respond to estrogen, such as e.g., vagina, vulva, uterus, bladder, urethra, breasts, bones, heart, blood vessels, brain, skin, hair, mucous membranes, and the like. The most common symptom of menopause is a change in the menstrual cycle, but other symptoms may occur, including but not limited to e.g., hot flashes, night sweats, insomnia, mood swings/irritability, memory or concentration problems, vaginal dryness, heavy bleeding, fatigue, depression, hair changes, headaches, heart palpitations, sexual disinterest, urinary changes and weight gain.

Menopause may be marked by the final period or ovulation cycle of the female subject, but is generally not an abrupt event, rather a gradual process. The clearest indication of menopause is the absence of an ovulation for one year, at which point a woman may be referred to as postmenopausal. It is also possible to diagnose menopause by testing hormone levels. One important test measures the levels of follicle-stimulating hormone (FSH), which steadily increases as a woman ages.

The age of menopause onset as well as the age of menopause completion may vary. Eight out of every 100 women will stop menstruating before age 40 and five out of every 100 women will continue to have periods until they are about 60 years of age. The average age of menopause is 51 and often occurs between the ages of 45 and 55. Menopause before the age of 40 may be referred to as premature menopause. Menopause before the age of 45 may be referred to as early menopause.

Some factors may be useful in predicting the onset and/or completion of menopause including but not limited to e.g., family history, body type, and lifestyle choices. The age at which menstruation began is not necessarily a predictor of when menopause will occur. For example, a woman beginning menstruation early or having entered puberty early will not necessarily experience early menopause.

The term "premenopause" generally refers to menstrual cycling that is relatively normal for a subject. A subject in premenopause may experience some gradual change in menstruation across a lifecycle, such as alteration in cycle length, changes in period pain or other premenstrual symptoms. However, during premenopause, on average, menstrual cycling will occur at regular intervals, including about monthly. The length of menstrual cycles may vary and may range from 21 to 45 days including 21 to 35 days in women of reproductive age, where the average cycle is 28 days.

The terms "perimenopause" or "menopausal transition" may be used interchangeably and generally refer to the interval in which many woman begin to experience one or more symptoms of menopause including e.g., irregular menstrual cycles. Perimenopause generally refers to the period just before menopause.

Further definitions and information related to menopause, including pre- and post-menopause may be found in Menopause: Full Guideline. NICE Guideline, No. 23. National Collaborating Centre for Women's and Children's Health (UK). London: National Institute for Health and Care Excellence (UK); 2015 Nov. 12; the disclosure of which is incorporated herein by reference in its entirety.

Whereas infertility and/or menopause, including premature menopause and early menopause, may not be classically considered diseases per se, for simplicity reference to diseases made herein will include fertility related conditions such as infertility, menopause, premature menopause, early menopause, and the like.

The terms "pluripotent progenitor cells", "pluripotent progenitors", "pluripotent stem cells", "multipotent progenitor cells" and the like, as used herein refer to cells that are capable of differentiating into two or more different cell types and proliferating. Non limiting examples of pluripotent precursor cells include but are not limited to embryonic stem cells, blastocyst derived stem cells, fetal stem cells, induced pluripotent stem cells, ectodermal derived stem cells, endodermal derived stem cells, mesodermal derived stem cells, neural crest cells, amniotic stem cells, cord blood stem cells, adult or somatic stem cells, neural stem cells, bone marrow stem cells, bone marrow stromal stem cells, hematopoietic stem cells, lymphoid progenitor cell, myeloid progenitor cell, mesenchymal stem cells, epithelial stem cells, adipose derived stem cells, skeletal muscle stem cells, muscle satellite cells, side population cells, intestinal stem cells, pancreatic stem cells, liver stem cells, hepatocyte stem cells, endothelial progenitor cells, hemangioblasts, gonadal stem cells, germline stem cells, and the like. Pluripotent progenitor cells may be acquired from public or commercial sources or may be newly derived. As described herein, in some instances, pluripotent progenitor cells of the subject disclosure are those cells capable of giving rise to ovarian cells or derivatives, including e.g., oogonia.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-19}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The terms "antibody" and "immunoglobulin", as used herein, are used interchangeably may generally refer to whole or intact molecules or fragments thereof and modified and/or conjugated antibodies or fragments thereof that have been modified and/or conjugated. The immunoglobulins can be divided into five different classes, based on differences in the amino acid sequences in the constant region of the heavy chains. All immunoglobulins within a given class will have very similar heavy chain constant regions. These differences can be detected by sequence studies or more commonly by serological means (i.e. by the use of antibodies directed to these differences). Immunoglobulin classes include IgG (Gamma heavy chains), IgM (Mu heavy chains), IgA (Alpha heavy chains), IgD (Delta heavy chains), and IgE (Epsilon heavy chains).

Antibody or immunoglobulin may refer to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized, see for instance *Fundamental Immunology* Ch. 7 (Paul, W., ed., 2nd ed. Raven Press, N.Y. (1989)). Briefly, each heavy chain typically is comprised of a heavy chain variable region (abbreviated as $V_H$) and a heavy chain constant region (abbreviated as $C_H$). The heavy chain constant region typically is comprised of three domains, $C_H1$, $C_H2$, and $C_H3$. Each light chain typically is comprised of a light chain variable region (abbreviated as $V_L$) and a light chain constant region (abbreviated herein as $C_L$). The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs).

Whole or largely intact antibodies are generally multivalent, meaning they may simultaneously bind more than one molecule of antigen whereas antibody fragments may be monovalent. Antibodies produced by an organism as part of an immune response are generally monospecific, meaning they generally bind a single species of antigen. Multivalent monospecific antibodies, i.e. antibodies that bind more than one molecule of a single species of antigen, may bind a single antigen epitope (e.g., a monoclonal antibody) or multiple different antigen epitopes (e.g., a polyclonal antibody).

Multispecific (e.g., bispecific) antibodies, which bind multiple species of antigen, may be readily engineered by those of ordinary skill in the art and, thus, may be encompassed within the use of the term "antibody" used herein where appropriate. Also, multivalent antibody fragments may be engineered, e.g., by the linking of two monovalent antibody fragments. As such, bivalent and/or multivalent antibody fragments may be encompassed within the use of the term "antibody", where appropriate, as the ordinary skilled artisan will be readily aware of antibody fragments, e.g., those described below, which may be linked in any convenient and appropriate combination to generate multivalent monospecific or polyspecific (e.g., bispecific) antibody fragments.

Antibody fragments include but are not limited to antigen-binding fragments (Fab or F(ab), including Fab' or F(ab'), (Fab)$_2$, F(ab')$_2$, etc.), single chain variable fragments (scFv or Fv), "third generation" (3G) molecules, etc. which are capable of binding the epitopic determinant. These antibody fragments retain some ability to selectively bind to the subject antigen, examples of which include, but are not limited to:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab)_2$, the fragment of the antibody that can be obtained by treating whole antibody with the enzyme pepsin without subsequent reduction;

(4) $F(ab)_2$ is a dimer of two Fab' fragments held together by two disulfide bonds;

(5) Fv, defined as a genetically engineered fragment containing the variable region of the light chain and the variable region of the heavy chain expressed as two chains;

(6) Single chain antibody ("SCA"), defined as a genetically engineered molecule containing the variable region of the light chain, the variable region of the heavy chain, linked by a suitable polypeptide linker as a genetically fused single chain molecule; such single chain antibodies may be in the form of multimers such as diabodies, triabodies, tetrabodies, etc. which may or may not be polyspecific (see, for example, WO 94/07921 and WO 98/44001) and (7) "3G", including single domain (typically a variable heavy domain devoid of a light chain) and "miniaturized" antibody molecules (typically a full-sized Ab or mAb in which non-essential domains have been removed).

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already inflicted (e.g., those with infertility, e.g. those having infertility) as well as those in which prevention is desired (e.g., those with increased susceptibility to infertility; those subject to premature menopause; those suspected of having infertility; etc.).

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

A "therapeutically effective amount", a "therapeutically effective dose" or "therapeutic dose" is an amount sufficient to effect desired clinical results (i.e., achieve therapeutic efficacy, achieve a desired therapeutic response, etc.). A therapeutically effective dose can be administered in one or more administrations. For purposes of this disclosure, a therapeutically effective dose of an agent that enhances fertility and/or compositions is an amount that is sufficient, when administered to the individual, to palliate, ameliorate, stabilize, reverse, prevent, slow or delay the progression or onset of infertility by, for example, increasing the number of oogonia present in the ovary of the subject.

The term "engraftment" as used herein refers to the transfer of cells produced by the methods described herein to a subject in need thereof. The graft may be allogeneic, where the cells from one subject are transferred to another subject; xenogeneic, where the cells from a foreign species are transferred to a subject; syngeneic, where the cells are from a genetically identical donor or an autograft, where the cells are transferred from one site to another site on the same subject. Accordingly, engraftment may also include the transfer of cells, obtained from a subject and subjected to treatment or culture outside of the subject, back into the subject, including into the same or a different location from which the cells were obtained.

DETAILED DESCRIPTION

Methods of enhancing fertility of a female subject by increasing the number of oogonia present in the ovary of the female subject are provided. Aspects of the methods include methods of in vivo expansion of oogonia as well as methods of ex vivo expansion of oogonia.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

METHODS

As summarized above, the methods of the present disclosure include methods of enhancing fertility of a female subject by increasing the number of oogonia present in the ovary of the female subject, including methods that involve in vivo expansion of oogonia and/or ex vivo expansion of oogonia. As such, the subject methods may include only in vivo expansion of oogonia, only ex vivo expansion of oogonia or combinations of methods of in vivo and ex vivo expansion of oogonia. Methods of the present disclosure may be performed alone or in combination with other methods directed at increasing fertility in a female subject.

The instant methods may involve increasing the number of oogonia present in the female ovary during various points in the life of the subject female organism. Non-limiting examples of timepoints during which the present methods may be employed to increase the number of oogonia include: during post-natal life, during a juvenile stage of life (e.g., during infancy, during childhood, during pre-adolescence, during adolescence, before reproductive maturity, etc.), during adulthood (e.g., during post-adolescence, during reproductive maturity, prior to menopause, during menopause, post-menopause, etc.).

In some instances, in vivo expansion of oogonia may be employed during one or more life stages of a subject including e.g., during post-natal life, during a juvenile stage of life (e.g., during infancy, during childhood, during pre-adolescence, during adolescence, before reproductive maturity, etc.), during adulthood (e.g., during post-adolescence, during reproductive maturity, prior to menopause, during menopause, post-menopause, etc.).

In some instances, ex vivo expansion of oogonia may be employed during one or more life stages of a subject including e.g., during post-natal life, during a juvenile stage of life (e.g., during infancy, during childhood, during pre-adolescence, during adolescence, before reproductive maturity, etc.), during adulthood (e.g., during post-adolescence, during reproductive maturity, prior to menopause, during menopause, post-menopause, etc.).

In some instances, in vivo and ex vivo expansion of oogonia may be employed during one or more life stages, including e.g., where the two approaches are employed during the same of different life stage. For example, in some instances, in vivo expansion may be employed first, followed by ex vivo expansion. In some instances, ex vivo expansion may be employed first, followed by in vivo expansion.

In Vivo Expansion of Oogonia

As summarized above, provided are methods of enhancing female fertility in a female subject through the use of in vivo expansion of oogonia. By "in vivo expansion" is generally meant that the desired cell type, e.g., oogonia, is expanded within a living subject. Methods of expanding a desired cell type within a living subject will vary and may include where the desired cell type is caused to proliferate, where a progenitor of the desired cell type is caused to proliferate, where a progenitor of the desired cell type is caused to differentiate into the desired cell type, where a cell type other than the desired cell type or a progenitor thereof is caused to differentiate into the desired cell type, where a cell type other than the desired cell type or a progenitor thereof is caused to differentiate into the progenitor of the desired cell type and the like, or combinations thereof.

In some instances, in vivo expansion of a desired cell type may include maintenance of the cells of the desired cell type, e.g., preventing death and/or differentiation and/or senescence of the desired cell type. In such instances, by preventing death and/or differentiation and/or senescence of a desired cell type the number of the desired cell type may be maintained or increased. In some instances, enhancing fertility of a subject may include increasing the production of a desired cell type (e.g., by differentiation, proliferation, etc.) as well as increasing the maintenance of the desired cell type. In some instances, enhancing fertility of a subject may include increasing the maintenance of the desired cell type without increasing the production of a desired cell type (e.g., by differentiation, proliferation, etc.).

Methods of interest for in vivo enhancing of oogonia include partially reprograming cells of the ovary to increase the number of oogonia present in the ovary of a female subject. Partial reprogramming does not result in the complete loss of differentiated cellular identity as is common in conventional methods of cellular reprogramming that are normally taken to completion. Cellular reprogramming generally refers to the complete reprogramming of differentiated cells (e.g., terminally differentiated cells) into a pluripotent (i.e., embryonic-like) state. Such reprogramming may be achieved through the forced expression of reprogramming factors, including e.g., at least three of the four factors that have commonly become known as the Yamanaka factors (e.g., Oct4, Sox2, Klf4 and c-Myc) or their corresponding orthologs in other species. Various methods of reprograming using the reprogramming factors have been developed, but generally such methods require the prolonged expression of or induction by the reprograming factors (e.g., the Yamanaka factors) for period of at least about a week, eventually leading to the complete loss differentiated cellular identity and the formation of induced pluripotency stem cell (iPSC) colonies in the following days to weeks (see Malik & Rao. Methods Mol Biol. (2013) 997:23-33; the disclosure of which is incorporated herein by reference in its entirety).

Others have demonstrated that other transcription factors may be employed in transforming or reprogramming adult cells. These other transcription factors include, e.g., Lin28, Nanog, hTert and SV40 large T antigen as described, for example, by Takahashi et al., 2006 Cell, 126: 663-676 and Huiqun Yin, et al. 2009, Front. Agric. China 3(2): 199-208, incorporated by reference herein.

In contrast to complete cellular reprogramming, e.g., as used to generate iPS cells, partial reprograming involves one or more short periods of exposure to the reprograming factors or a subset thereof. For example, in partial reprograming techniques, cells may be subjected to the influence of one or more reprogramming factors for a period of less than one week, including but not limited to e.g., less than one day to six days, including e.g., 12 hours to 6 days, 1 to 6 days, 2 to 6 days, 3 to 6 days, 12 hours to 5 days, 1 to 5 days, 2 to 5 days, 3 to 5 days, 12 hours to 4 days, 1 to 4 days, 2 to 4 days, 3 to 4 days, 12 hours to 3 days, 1 to 3 days, 2 to 3 days, 12 hours to 2 days, 12 hours to 1 day, 12 hours, 1 day, 2 days, 3 days, 4 days, 5 days, 6 days, etc. The length of time of induction of reprogramming factors will be a time period that does not lead to complete reprogramming and/or does not result in tumor formation.

Partial reprogramming in the present methods may include a single period of reprograming factor induction or multiple periods, including but not limited to e.g., 2 or more periods, 3 or more periods, 4 or more periods, 5 or more periods, 6 or more periods, 7 or more periods, 8 or more periods, 9 or more periods, 10 or more periods, etc. Induction of reprograming factors may be performed continuously or non-continuously (i.e., intermittently). In intermittent induction, a period of no induction may be introduced between periods of induction, such that an "on" period of induction is followed by an "off" period of induction, which may e.g., be followed by another "on" period. The length of a subject period of no induction may vary, including where the length is the equal or unequal to or longer or shorter than the length of the period of induction. In some instances, the length of a period of no induction, expressed as a percentage of the length of the corresponding period of induction, may range from less than 10% to 1000% or more, including but not limited to e.g., 10%, 25%, 33%, 50%, 66%, 75%, 100%, 150%, 200%, 250%, 300%, 350%, 400%, 450%, 500%, 550%, 600%, 650%, 700%, 750%, 800%, 850%, 900%, 950%, 1000%, etc.

Cycles of "on" and "off" periods of reprograming factor induction will vary in protocols for partial reprogramming. For example, a partial reprogramming schedule may include multiple cycles, where a cycle is defined as a pair of "on" and "off" periods, including but not limited to e.g., 2 or more cycles, 3 or more cycles, 4 or more cycles, 5 or more cycles, 6 or more cycles, 7 or more cycles, 8 or more cycles, 9 or more cycles, 10 or more cycles, etc. In some instances, cycles may be performed for an acute period. In some instances, cycles may be performed chronically.

In some instances, a reprogramming schedule may include one or more holiday periods, where a holiday period is defined as a period where no partial reprogramming is performed, i.e., a period where no partial reprogramming cycle is performed. Such holiday periods will vary and may range from 1 week or more, including but not limited to e.g., 1 week, 2 weeks, 3 weeks, a month, 2 months, 3 months, 4 months, 5 months, 6 months, 7 months, 8 months, 9 months, 10 months, 11 months, 1 year, 1.25 years, 1.5 years, 1.75 years, 2 years, 2.5 years, 3 years, 3.5 years, 4 years, 4.5 years, 5 years, etc.

In vivo partial reprograming will generally include enhancing the activity of a reprogramming factor. The term a "reprogramming factor," as used herein, refers to a developmental potential altering factor, as that term is defined herein, such as a gene, protein, RNA, DNA, or small molecule, the expression of which contributes to the reprogramming of a cell, e.g. a somatic cell, to a less differentiated or undifferentiated state, e.g. to a cell of a pluripotent state or partially pluripotent state. A reprogramming factor can be, for example, transcription factors that can reprogram cells to a pluripotent state, such as SOX2, OCT3/4, KLF4, NANOG, LIN-28, c-MYC, and the like, including as any gene, protein, RNA or small molecule, that can substitute for one or more of these in a method of reprogramming cells. Useful methods of partial reprogramming may also include those described in Ocampo et al. Cell. (2016) 167:1719-1733; the disclosure of which is incorporated herein by reference in its entirety. A reprogramming factor can also be termed a "de-differentiation factor," which refers to a developmental potential altering factor, as that term is defined herein, such as a protein or RNA, that induces a cell to de-differentiate to a less differentiated phenotype, that is, a de-differentiation factor increases the developmental potential of a cell.

By "enhancing the activity of" is generally meant that the activity of the factor is increased, e.g., by increasing the endogenous expression of the factor, ectopically or heterologously expressing the factor, increasing the amount of the factor present in the cell, inhibiting an inhibitor of the factor, increasing the activity or expression of an activator of the factor, and the like. In some instances, enhanced activity of a factor may be measured, by any convenient means, e.g., to verify that the activity of the factor has been enhanced. Non-limiting examples of methods of measuring such enhanced activity include e.g., measuring the amount of the factor, measuring the expression of a nucleic acid encoding the factor, measuring the expression of downstream targets of the factor, measuring the amount or expression of a reporter configured to correlate with the amount or expression of the factor (e.g., a protein reporter such as e.g., a detectable protein, such as e.g., a fluorescent protein), and the like.

In some instances, the degree of partial reprogramming may serve as a measure of enhanced reprogramming factor activity. Any convenient method of assessing the degree of partial reprogramming of a cell may be employed including e.g., the expression of particular histone variants (e.g., gamma-H2AX downregulation), the expression of multipotency markers (e.g., Oct4), the expression of stress response genes (e.g., p16 down regulation, p21 downregulation, Atf3 downregulation, Gadd45b downregulation, etc.) the expression of senescence markers (e.g., MMP13 downregulation, etc.), monitoring epigenetic modifications (e.g., Histone H3 methylated Lys9 (H3K9), etc.), monitoring proliferation (phosphorylated histone H3 (H3P), Ki67, cyclins, etc.) and the like.

Enhancing the activity of a reprogramming factor may include inducing reprograming factors (e.g., the Yamanaka factors, or a subset thereof) in a subject for a period of time insufficient to cause complete reprogramming. Accordingly, a subject may be administered an amount of an agent sufficient to induce activation of, e.g., Oct4, Sox2, KI4 and/or c-Myc, and sub-combinations thereof, or the corresponding ortholog(s) in the relevant specie being treated. Any convenient technique for inducing activity, in vivo, of individual reprograming factors may be employed. For example, in some instances, the subject may be administered a vector (e.g., a viral vector, a non-viral vector, and the like) containing a nucleic acid encoding for one or more reprogramming factors, e.g., Oct4 protein, Sox2 protein, Klf4 protein, c-Myc protein, etc. In some instances, the cells to be partially reprogrammed may be transduced with one or more of Oct4 protein, Sox2 protein, Klf4 protein and/or c-Myc protein; including e.g., where the subject proteins are engineered with an attached protein transduction domain, administered with a transduction reagent, or the like.

Various vectors may be employed to introduce a reprogramming factor, including, e.g., an RNA such as mRNA, microRNA, siRNA, antisense RNA, a protein and combinations thereof, into a cell. Expression vectors that may be employed include, e.g., a retrovirus, a lentivirus, an adenovirus, an adeno associated virus, a herpes virus, a Sindbis virus, a pox virus, a baculovirus, a bacterial phage, a Sendai virus and combinations thereof. In some instances, an employed vector is a non-replicative vector such as, e.g., Sendai virus vectors engineered to be nonreplicative. In some instances, non-replicative vectors, while incapable of replication, remain capable of productive expression of nucleic acids encoding protein(s) carried by the vector, thereby preventing any potential uncontrolled spread to other cells or within the body of a subject.

Also, examples of artificial chromosome vectors that can be used include human artificial chromosome (HAC), yeast artificial chromosome (YAC), and bacterial artificial chromosome (BAC and PAC) vectors. As a plasmid, a plasmid for mammalian cells can be used (e.g., Okita K, et al., Science 322: 949 (2008)). A vector can contain regulatory sequences such as a promoter, an enhancer, a ribosome binding sequence, a terminator, and a polyadenylation site, so that a reprogramming factor can be expressed. A vector may further contain, if desired, a selection marker sequence such as a drug resistant gene (e.g., a neomycin resistant gene, an ampicillin resistant gene, and a puromycin resistant gene), a thymidine kinase gene, and a diphtheria toxin gene, a reporter gene sequence such as a green fluorescent protein (GFP), beta-glucuronidase (GUS), FLAG, or combinations thereof. Also, the above vector may have LoxP sequences located before and after the segment encoding the reprogramming factor to permit cleavage at the ends of the reprogramming factor segment (before and after) or at both ends of the segment encoding a promoter and the reprogramming factor after introduction into the mammalian cells.

In some instances, a subject may be administered an effective amount of a partial reprogramming composition, where such amount is effective to partially reprogram cells of the ovary to increase the number of oogonia present in the ovary. As summarized above, the reprogramming composition may be administered chronically or acutely including, where the administering is performed according to a predetermined schedule (i.e., a treatment schedule).

Suitable routes of administration include, but are not limited to e.g., oral, intravenous, rectal, aerosol, parenteral, ophthalmic, pulmonary, transmucosal, transdermal, vaginal, optic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections. The partial reprogramming composition may be administered systemically or locally.

Systemic administration may include introduction of the composition into the blood flow of the subject. Any convenient route of introducing an agent into the blood flow may be employed including but not limited to e.g., intravenous injection, transdermal administration (e.g., a cream or transdermal patch containing the composition), intramuscular injection, and the like. Other routes of systemic administration include e.g., oral, inhalation, suppository, and the like. Systemic administration will generally involve enteral or parenteral routes of administration.

Local administration may include locally administering the composition to the reproductive organs of the subject, including e.g., administering the composition to the ovary or ovaries of the subject. Methods of local administration will vary and may include e.g., topically applying the composition to the desired area or implanting or injecting the composition into the desired area. For example, in some instances, local administration may include surgically (including e.g., orthoscopically) applying the composition to a desired location (e.g., the ovary). Local administration may also include direct injection of the composition on or into the ovary, with or without assistive imaging (e.g., ultrasound) to target the ovary. In some instances, local delivery may involve the implantation of a drug delivery device into a desired location (e.g., ovary), where, following implantation the device locally delivers the composition to cells or tissues of the desired location. Useful locations within the female reproductive tract for local delivery include but are not limited to e.g., the ovary, the uterus, the vagina, the uterine tubes, the ovarian artery, the ovarian vein, and the like.

The subject methods of partial reprogramming may affect any cell or combination of cells (e.g., tissue) of the female reproductive tract, including e.g., ovarian cells. Ovary cell types include cells present in one or more ovary regions including e.g., the ovarian cortex, ovarian medulla or germinal epithelium. Specific ovary cell types that may be affected include e.g., oogonia, germinal epithelium cells, ovarian stem cells, primordial follicle cells, primary follicle cells, secondary follicle cells, vesicular follicle cells, oocytes, theca cells, granulosa cells, ovarian stromal cells and corpus luteum cells.

Ovary cell types may express one or more ovary lineage markers. Useful ovarian lineage markers include those expressed during development of the ovary as well as in adult ovarian tissue. Ovarian lineage markers may include e.g., germline markers (e.g., Oct4, Mvh, Dazl, Blimp1, Fragilis, Stella, Rex1, etc., including human homologs thereof), germ cell-specific markers (e.g., germ cell nuclear antigen (GCNA), cKIT, mouse vasa homolog (MVH), etc., including human homologs thereof), ovary-specific markers whether expressed during development and/or during juvenile and/or adult stages (e.g., Oocyte-G1, Zp3 (zona pellucida sperm binding protein 3), Nobox (newborn ovary homeobox protein), and Gdf9 (growth differentiation factor 9), etc., including human homologs thereof), ovarian stroma markers (e.g., COUP-TFII/NR2F2, etc., including human homologs thereof), granulosa cell and granulosa precursor cell markers (e.g., FOXL2, leucine-rich repeat-containing G protein-coupled receptor 5 (LGR5), etc., including human homologs thereof), ovarian surface epithelium markers (e.g., lymphocyte antigen 6 complex, locus A (LY6A) etc., including human homologs thereof), stem cell markers (e.g., NANOG, secreted frizzled related protein 1 (SFRP1), LIM homeobox 9 (LHX9), ALDH1A1, ALDH1A2, etc., including where stem cell markers are expressed in the ovarian surface epithelial), oocyte-specific markers (e.g., DAZL, VASA, STELLA, ZP, GDF9B, SCP3, C-MOS, etc., including human homologs thereof), endothelial-like markers (e.g., TIE (tyrosine kinase with Ig-like and epidermal growth factor [EGF]-like domains), TEK (endothelial-specific receptor tyrosine kinase), von Willebrand factor, cKIT, CD31, FLT-1 (VEGF receptor 1), etc., including human homologs thereof), endothelial markers (e.g., CD14, CD45, CD133, VEGF-R2, etc., including human homologs thereof), granulosa-like cell markers (e.g., FOXL2, CYP19A1, FSHR, AMH (anti-Müllerian hormone), AMHR2, etc., including human homologs thereof), those markers described in Hummitzsch et al., Endocr Rev. 2015 February; 36(1): 65-91; the disclosure of which is incorporated herein by reference in its entirety. Useful ovary lineage markers identifying ovary cell types also include but are not limited to e.g., Lgr5, FOXL2, NR2F2 and those described in e.g., Rastetter et al. (Dev Biol. 2014 Oct. 15; 394(2):242-52) and the human homologs thereof.

Methods of in vivo partial reprogramming may include specific targeting of ovarian cells. For example, in some instances, a partial reprogramming vector (i.e., a vector inducing expression of one or more reprogramming factors) may be specifically engineered to target an ovarian cell type. Engineered vectors for cell specific targeting include vectors based on lentiviruses or adeno-associated viruses that have been engineered such that they use a cell surface marker of choice for cell entry instead of their natural receptors. Binding to the surface marker is mediated by a targeting ligand displayed on the vector particle surface, which can be a peptide, single-chain antibody, or designed ankyrin repeat protein or the like. In some instances, useful surface markers may include an ovary lineage marker expressed on the surface of a targeted cell.

In some instances, the present methods may include in vivo partial reprogramming of ovarian stem cells. In some instances, the subject methods may specifically partially reprogram ovarian stem cells. Specific targeting of ovarian stem cells may employ targeting of ovarian stem cell markers and/or stem cell and/or germline markers expressed in the ovaries such as e.g., VASA, NANOS, homologs and/or orthologs thereof, and the like (see e.g., Hana et al., Fertil Steril (2014) 101:20-30; White et al. Nat Med. (2012) 18(3):413-421; Woods et al. Reproductive Sciences (2013) 20(1):7-15; the disclosures of which are incorporated herein by reference in their entirety). In some instances, specific partial reprogramming of ovarian stem cells may include local administration of a partial reprogramming composition.

Ex Vivo Expansion of Oogonia

As summarized above, provided are methods of enhancing female fertility in a female subject through the use of ex vivo expansion of oogonia. By "ex vivo expansion" is generally meant that the desired cell type, e.g., oogonia, is expanded outside of a living subject. Methods of expanding a desired cell type outside a living subject will vary and may include where the desired cell type is caused to proliferate in a culture system, where a progenitor of the desired cell type is caused to proliferate in a culture system, where a progenitor of the desired cell type is caused to differentiate into the desired cell type in a culture system, where a cell type other than the desired cell type or a progenitor thereof is caused to differentiate into the desired cell type in a culture system, where a cell type other than the desired cell type or a progenitor thereof is caused to differentiate into the progenitor of the desired cell type in a culture system, and the like or combinations thereof.

In some instances, ex vivo expanded oogonia are derived from primary oogonia derived from the ovary. In some instances, ex vivo expanded oogonia are derived from a progenitor cell derived from the ovary. Useful ovarian progenitor cells include e.g., ovarian stem cells. Ovarian stem cells include those described in Hana et al., Fertil Steril (2014) 101:20-30; White et al. Nat Med. (2012) 18(3):413-421; Woods et al. Reproductive Sciences (2013) 20(1):7-15; the disclosures of which are incorporated herein by reference in their entirety. Progenitor cells from which oogonia may be expanded include those autologously derived or those allogenic to the eventual female recipient.

In addition, useful progenitor cells of ex vivo expansion and manipulation will include those that are naturally present in the female ovary as well as those that are derived by one or more in vitro methods including e.g., cellular reprogramming of non-progenitor cells into ovarian cell progenitors. For example, in some instances, a progenitor cell may be isolated from the ovary of a subject and expanded ex vivo according to the methods described herein. In other instances, a non-progenitor cell may be isolated from a subject (or may have been previously isolated from a subject, e.g., in the case of banked tissue), reprogramed into an ovarian progenitor cell fate and expanded ex vivo according to the methods described herein.

As summarized above, cells of the subject methods may be autologously derived. By autologously derived it is meant that the cells are derived from the subject that is to be treated with the cells. The cells may be derived from a tissue sample obtained from the subject including but not limited to, e.g., an ovarian tissue sample, and the like. In some instances, the sample from which cells are derived may be a biopsy or swab, e.g., a biopsy or swab collected to diagnose, monitor, or otherwise evaluate the subject, e.g., diagnose the subject for infertility or a reproductive disease or other disease of the reproductive system, e.g., ovarian cancer, ovarian cyst, polycystic ovary syndrome, premature ovarian failure, surface epithelial-stromal tumor, Brenner tumor, follicular cyst of ovary, ovarian torsion, ovarian disease, luteoma, hypogonadism, ovarian hyperthecosis, endometriosis of the ovary, ovarian hyperstimulation syndrome, Sertoli-Leydig cell tumor, etc., or for cell collection. In some instances, the autologous sample from which the cells are derived may be a previously collected and stored sample, e.g., a banked tissue sample, from the subject to be treated, including but not limited to e.g., banked cardiac tissue or cells, banked musculoskeletal tissue or cells, banked reproductive tissue or cells, banked skin tissue or cells, banked bone tissue or cells, banked bone marrow tissue or cells, banked vascular tissue or cells, banked umbilical cord blood tissue or cells, and the like.

In some instances, cells of the subject methods may be non-autologously derived. By non-autologously derived it is meant that the cells are not derived from the subject that is to be treated with the cells. In some instances, non-autologously derived cells may be xeno-derived (i.e., derived from a non-human animal) or allo-derived (i.e. derived from a human donor other than the subject to be treated). Non-autologously derived cells or tissue may be derived from any convenient source of cells or tissue collected by any convenient means.

Whether to use autologously derived or non-autologously derived cells may be determined according to the discretion of the subject's clinician and may depend on, e.g., the health, age, genetic predisposition or other physical state of the subject. In some instances, autologous cells may be preferred, including, e.g., to decrease the risk or immune rejection of the transplanted cells. In some instances, non-autologous cells may be preferred, including, e.g., when the subject has a genetic defect.

In some instances, the derived or obtained cells are prepared, dissociated, and/or maintained in culture prior to being ex vivo expanded as described herein. In some instances, before ex vivo expansion the cells (e.g., as obtained from a subject) are dissociated, e.g., to generate a single-cell suspension. In some instances, the dissociation of the cells is chemical, molecular (e.g., enzyme mediated), or mechanical dissociation. Methods of chemical, molecular, and/or enzyme mediated dissociation will vary and in some instances may include but are not limited to the use of, e.g., trypsin, TrypLE Express™, TrypLE Select™, Accutase®, StemPro® (Life Technologies, Inc., Grand Island, N.Y.), calcium and magnesium free media, low calcium and magnesium medium, and the like. In some instances the dissociation media may further include pro-survival factors including but not limited to, e.g., Rho-associated kinase (ROCK) inhibitor, pinacidil, allopurinol, uricase, cyclosporine (e.g., low does, i.e., sub-immunosuppressive dose, cyclosporine), ZVAD-fmk, pro-survival cytokines (e.g., insulin-like growth factor-1 (IGF-1)), Thiazovivin, etc.

In some instances, methods of culturing cells may include xeno-free culture conditions wherein, e.g., human cells are not cultured with any reagents derived from non-human animals. In some instances, methods culturing of cells include feeder-free culture conditions, wherein the cells are cultured under conditions that do not require feeder cells and/or in feeder cell free medium, including e.g., commercially available feeder-free mediums, such as, e.g., those available from STEMCELL Technologies, Inc. (Vancouver, BC). In some instances, methods culturing of cells include culture conditions that include supplemental serum, including e.g. supplement of autologously derived serum, e.g., as described in Stute et al. (2004) *Exp Hematol,* 32(12):1212-25. In some instances, methods of culturing of cells or derivatives thereof include culture conditions that are serum-free, meaning the culture media does not contain animal, mammal, or human derived serum. Serum-free culture conditions may be performed for only a portion of the life of the culture or may performed for the entire life of the culture.

Cells may be cultured in two dimensional or three dimensional formats (e.g., on non-coated or coated surfaces or within a solid or semi-solid matrix). In some instances the cell media may include one or more pro-survival factors, e.g., including those described herein. General methods of culturing human pluripotent cells are described in, e.g., Freshney et al. (2007) *Culture of human stem cells,* Wiley-Interscience, Hoboken, N.J. and Borowski et al. (2012) *Basic pluripotent stem cell culture protocols,* StemBook, ed. The Stem Cell Research Community, StemBook, doi/10.3824/stembook, the disclosures of which are incorporated herein by reference.

In some instances, culture of ovarian pluripotent progenitors (e.g., ovarian stem cells, oogonia and the like), regardless of the method employed in their derivation, may involve cell-aggregate culture. By "cell-aggregate culture" is generally meant the cells are cultured under conditions that promote 3D cell aggregate formation. Without being bound by theory, cell-aggregate culture may provide cell-cell contacts between cells that promote survival and/or proliferation of the desired cell type. Such interactions may recapitulate progenitor cell-progenitor cell interactions and/or niche interactions that stimulate progenitor cell maintenance and may, in some instances, be present in the natural progenitor cell niche.

Culture conditions that promote cell aggregate formation may include e.g., culturing the cells in a low-attachment culture vessel (e.g., a plate, dish, flask, well of a multi-well device, and the like). Low-attachment culture surfaces include surfaces that are hydrophilic and/or neutrally charged. In some instances, low attachment surfaces may be coated to prevent cell attachment, including e.g., hydrogel coated. Low-attachment surfaces/coatings are generally, but not necessarily, stable, non-cytotoxic, biologically inert and/or non-degradable.

In cell-aggregate culture the cultured cells may transition from dissociated cells, in suspension or in 2D culture, into 3D culture in cell aggregates. In some instances, cells cultured in aggregates may not be fully dissociated prior to aggregate culture. For example, a tissue (e.g., an ovary) may be only partially dissociated into cell clumps and the resulting clumps may be cultured under cell-aggregate culture conditions. Cell-aggregate cultures may include a single cell type only (e.g., only a desired pluripotent progenitor cell type) or may include a desired cell type and one or more additional cell types. For example, in some instances, an aggregate cell culture of a desired cell type (e.g., an ovarian pluripotent progenitor cell or oogonia) may be cultured with one or more undesired cell types, where the undesired cell types may provide a supportive role in the culture of the primary desired cell type. In some instances, undesired cells of a cell-aggregate culture may include cells of a lineage similar to that of the desired cells. For example, where desired ovarian pluripotent progenitor cells or oogonia are cultured in an cell-aggregate culture, such cells may be combined with one or more undesired ovarian lineage cell types.

Ovarian-lineage cell types include cells present in one or more regions of the developed ovary including e.g., the ovarian cortex, ovarian medulla or germinal epithelium. Specific ovary cell types include e.g., oogonia, germinal epithelium cells, ovarian stem cells, primordial follicle cells, primary follicle cells, secondary follicle cells, vesicular follicle cells, oocytes, theca cells, granulosa cells, ovarian stromal cells and corpus luteum cells.

Methods of ex vivo expansion of oogonia and/or ovarian progenitors useful in the expansion of oogonia may include contacting the culture with one or more agents that promote the survival, growth, expansion and/or prevent or promote the differentiation and/or dedifferentiation of the cells in culture. Useful such agents include but are not limited to growth factors, small molecules and the like. Non-limiting examples of useful growth factors and small molecules (including non-limiting exemplary culture concentrations) include: Activin A (5 ng/ml, 20 ng/ml, 100 ng/ml), TGF-β1 (10 pg/ml, 50 pg/ml), SB431542 (2 uM, 10 uM), A83-01 (0.2 uM, 1 uM), BMP2 (20 ng/ml, 100 ng/ml), BMP4 (5 ng/ml, 20 ng/ml, 100 ng/ml), LDN-193189 (50 nM, 100 nM, 200 nM), DMH1 (1 uM, 10 uM), Wnt3a (10 ng/ml, 50 ng/ml), CHIR99021 (0.5 uM, 1 uM, 2 uM), IWR-1 (2.5 uM, 5 uM, 50 uM), IWP-2 (5 uM, 20 uM, 50 uM), PD0325901 (1 uM), FGF9 (200 ng/ml), FGF20 (100 ng/ml), FGF8 (100 ng/ml), FGF10 (100 ng/ml), EGF (100 ng/ml), BMP8a (100 ng/ml), SCF (100 ng/ml), IGF-1 (100 ng/ml), IGF-2 (10 ng/ml), LIF (1 ng/ml, 5 ng/ml, 10 ng/ml), Retinoic Acid (all trans) (0.1 uM, 1 uM), TTNPB (0.1 uM, 1 uM), BMS 195614 (1 uM), MM 11253 (1 uM), LE 135 (1 uM), Trichostatin A (200 nM), 5-Azacytidine (1 uM), SP600125 (10 uM), SB202190 (5 uM), Go6983 (5 uM), DAPT (5 uM), Purmorphamine (1 uM), KAAD-Cyclopamine (20 nM), and the like.

In some instances, useful culture conditions may include one or more of the following components: DMEM, F12, GlutaMAX, MEM NEAA, 2-Mercaptoethanol, antibiotic (e.g., Pen Strep), B-27 Supplement, ITS Liquid Media Supplement, BMP-7, FGF-2, Heparin, Y-27632, LIF, CHIR99021, LDN193189 and A83-01. In some instances, useful culture conditions, in whole or in part, may include those described in Li et al., Cell Stem Cell (2016) 19:1-14 and Tanigawa et al., Cell Rep. (2016) S2211-1247(16) 30365-5; the disclosures of which are incorporated herein by reference in their entirety.

Ex vivo expansion cultures may be propagated for any convenient length of time depending on various factors including but not limited to e.g., the desired degree of expansion, the size and/or source of the initial starting cell population, clinical considerations, including e.g., time necessary to prepare the recipient to receive the expanded cells, and the like. Accordingly, the length of time of ex vivo culture may vary and may range from less than three days to three weeks or more, including but not limited to e.g., 3 days to 3 weeks, 3 days to 2 weeks, 3 days to 1 week, 4 days to 3 weeks, 4 days to 2 weeks, 4 days to 1 week, 5 days to 3 weeks, 5 days to 2 weeks, 5 days to 1 week, 6 days to 3 weeks, 6 days to 2 weeks, 1 week to 2 weeks, 1 week to 3 weeks, 2 weeks to 3 weeks, and the like.

Following ex vivo expansion, the expanded cells may be transplanted into a subject, as described in more detail below. In some instances, the expanded cells may be transplanted in the ovary of the female subject, including e.g., where the cells are transplanted into one ovary or both ovaries of the subject. The cells may be delivered in an effective amount, including where such an amount is a therapeutically effective dose, or doses, sufficient to enhance the fertility of the subject.

Treatment Methods

As summarized above, the provided methods may enhance fertility of a female subject by increasing the number of oogonia present in the ovary of the female subject, where such methods may include e.g., in vivo expansion of oogonia and/or ex vivo expansion of oogonia. As such the methods of the present disclosure may include administering a single agent or a combination of agents, or therapeutic methods, directed to increasing the fertility of a subject. Accordingly, in some instances, the methods described include the sole use or sole administration of any of the agents described herein, whether described individually or as part of a combination therapy. In addition, any combination of any agents or therapies described herein may be employed in the subject methods.

In some instances, a single (i.e., only, sole) agent is administered to the subject for enhancing fertility in the subject. In some instances, administration of a single agent may be sufficient and clinically beneficial to enhance fertility. In some instances, an agent is administered as a monotherapy and is the single (i.e., only, sole) active agent administered to the subject for treating the condition. Medications that are not necessarily excluded from administration to the subject when an agent is administered as a monotherapy include, by way of non-limiting examples, medications for other purposes such as palliative care or comfort (e.g., aspirin, acetaminophen, ibuprofen, or prescription pain-killers; anti-itching topical medications) or for treating a different disease or condition, especially if the other medications are not agents for increasing fertility.

In some instances, an agent may be administered in combination with one or more additional agents. The individual agents of a combination therapy may be administered in series or may be administered simultaneously, including e.g., where the agents are combined in a cocktail. In some instances, a combination therapy (e.g., a combination of agents) agent is administered to the subject for enhancing fertility in the subject. In some instances, administration of a combination therapy (e.g., a combination of agents) may be sufficient and clinically beneficial to enhance fertility. In some instances, a combination therapy (e.g., a combination of agents) is administered as a cocktail and the agents of the cocktail are the only (i.e., sole) active agents administered to the subject for treating the condition.

Treatment of subjects to enhance fertility may include only methods directed to in vivo expansion of oogonia. For example administering to a subject only agents that expand oogonia in vivo, including e.g., administering to a subject only agents or a composition of agents for partial reprograming, as described in detail above.

Treatment of subjects to enhance fertility may include only methods directed to ex vivo expansion of oogonia. For example, expanding oogonia ex vivo and administering to a subject only the ex vivo expanded oogonia.

As described above, following ex vivo expansion, the expanded cells may be transplanted into a subject. In some instances, the expanded cells may be transplanted in the ovary of the female subject, including e.g., where the cells are transplanted into one ovary or both ovaries of the subject. The cells may be delivered in an effective amount, including where such an amount is a therapeutically effective dose, or doses, sufficient to enhance the fertility of the subject.

A "therapeutically effective dose" or "therapeutic dose" is an amount sufficient to effect desired clinical results (i.e., achieve therapeutic efficacy) or reduce, alleviate, or prevent symptoms to a desired extent as determined by the patient or the clinician. A therapeutically effective dose can be administered in one or more administrations. For purposes of this disclosure, a therapeutically effective dose of cells (e.g., oogonia or precursors thereof, and the like) and/or compositions (e.g., oogonia cell compositions, oogonia progenitor compositions, and the like) is an amount that is sufficient, when administered to (e.g., transplanted into) the individual, to palliate, ameliorate, stabilize, reverse, prevent, slow or delay the progression of the disease state (e.g., infertility, etc.) by, for example, enhancing fertility in the subject by increasing the number of oogonia.

In some embodiments, a therapeutically effective dose of cells (e.g., derived/expanded oogonia, etc.) is one cell or more (e.g., $1\times10^2$ or more, $5\times10^2$ or more, $1\times10^3$ or more, $5\times10^3$ or more, $1\times10^4$ cells, $5\times10^4$ or more, $1\times10^5$ or more, $5\times10^5$ or more, $1\times10^6$ or more, $2\times10^6$ or more, $5\times10^6$ or more, $1\times10^7$ cells, $5\times10^7$ or more, $1\times10^8$ or more, $5\times10^8$ or more, $1\times10^9$ or more, $5\times10^9$ or more, or $1\times10^{10}$ or more).

In some embodiments, a therapeutically effective dose of cells is in a range of from $1\times10^3$ cells to $1\times10^{10}$ cells (e.g., from $5\times10^3$ cells to $1\times10^{10}$ cells, from $1\times10^4$ cells to $1\times10^{10}$ cells, from $5\times10^4$ cells to $1\times10^{10}$ cells, from $1\times10^5$ cells to $1\times10^{10}$ cells, from $5\times10^5$ cells to $1\times10^{10}$ cells, from $1\times10^6$ cells to $1\times10^{10}$ cells, from $5\times10^6$ cells to $1\times10^{10}$ cells, from $1\times10^7$ cells to $1\times10^{10}$ cells, from $5\times10^7$ cells to $1\times10^{10}$ cells, from $1\times10^8$ cells to $1\times10^{10}$ cells, from $5\times10^8$ cells to $1\times10^{10}$, from $5\times10^3$ cells to $5\times10^9$ cells, from $1\times10^4$ cells to $5\times10^9$ cells, from $5\times10^4$ cells to $5\times10^9$ cells, from $1\times10^5$ cells to $5\times10^9$ cells, from $5\times10^5$ cells to $5\times10^9$ cells, from $1\times10^6$ cells to $5\times10^9$ cells, from $5\times10^6$ cells to $5\times10^9$ cells, from $1\times10^7$ cells to $5\times10^9$ cells, from $5\times10^7$ cells to $5\times10^9$ cells, from $1\times10^8$ cells to $5\times10^9$ cells, from $5\times10^8$ cells to $5\times10^9$, from $5\times10^3$ cells to $1\times10^9$ cells, from $1\times10^4$ cells to $1\times10^9$ cells, from $5\times10^4$ cells to $1\times10^9$ cells, from $1\times10^5$ cells to $1\times10^9$ cells, from $5\times10^5$ cells to $1\times10^9$ cells, from $1\times10^6$ cells to $1\times10^9$ cells, from $5\times10^6$ cells to $1\times10^9$ cells, from $1\times10^7$ cells to $1\times10^9$ cells, from $5\times10^7$ cells to $1\times10^9$ cells, from $1\times10^8$ cells to $1\times10^9$ cells, from $5\times10^8$ cells to $1\times10^9$, from $5\times10^3$ cells to $5\times10^8$ cells, from $1\times10^4$ cells to $5\times10^8$ cells, from $5\times10^4$ cells to $5\times10^8$ cells, from $1\times10^5$ cells to $5\times10^8$ cells, from $5\times10^5$ cells to $5\times10^8$ cells, from $1\times10^6$ cells to $5\times10^8$ cells, from $5\times10^6$ cells to $5\times10^8$ cells, from $1\times10^7$ cells to $5\times10^8$ cells, from $5\times10^7$ cells to $5\times10^8$ cells, or from $1\times10^8$ cells to $5\times10^8$ cells).

In some embodiments, the concentration of cells (e.g., derived/expanded oogonia, etc.) to be administered is in a range of from $1\times10^5$ cells/ml to $1\times10^9$ cells/ml (e.g., from $1\times10^5$ cells/ml to $1\times10^8$ cells/ml, from $5\times10^5$ cells/ml to $1\times10^8$ cells/ml, from $5\times10^5$ cells/ml to $5\times10^7$ cells/ml, from $1\times10^6$ cells/ml to $1\times10^8$ cells/ml, from $1\times10^6$ cells/ml to $5\times10^7$ cells/ml, from $1\times10^6$ cells/ml to $1\times10^7$ cells/ml, from $1\times10^6$ cells/ml to $6\times10^6$ cells/ml, or from $2\times10^6$ cells/ml to $8\times10^6$ cells/ml).

In some embodiments, the concentration of cells to be administered is $1\times10^5$ cells/ml or more (e.g., $1\times10^5$ cells/ml or more, $2\times10^5$ cells/ml or more, $3\times10^5$ cells/ml or more, $4\times10^5$ cells/ml or more, $5\times10^5$ cells/ml or more, $6\times10^5$ cells/ml or more, $7\times10^5$ cells/ml or more, $8\times10^5$ cells/ml or more, $9\times10^5$ cells/ml or more, $1\times^6$ cells/ml or more, $2\times10^6$ cells/ml or more, $3\times10^6$ cells/ml or more, $4\times10^6$ cells/ml or more, $5\times10^6$ cells/ml or more, $6\times10^6$ cells/ml or more, $7\times10^6$ cells/ml or more, or $8\times10^6$ cells/ml or more).

A therapeutically effective dose of cells may be delivered or prepared and any suitable medium, including but not limited to, e.g., those described herein. Suitable medium for the delivery of a therapeutically effective dose of cells will vary and may depend on, e.g., the type cells from which the effective dose of cells is derived or the type of derived cells of the effective dose. In some instances, a suitable medium may be a basal medium. "Cell medium" as used herein are not limited to liquid media may, in some instances, include non-liquid components or combinations of liquid media and non-liquid components. Non-liquid components that may find use a delivery or preparation medium include those described herein and those known in the art. In some instances, non-liquid components include natural or synthetic extra cellular matrix components.

In some instances, an effective dose of the cells described herein may be co-administered with one or more additional agents (e.g., prepared in a suitable medium). For example, an effective dose of derived oogonia may be co-administered with one or more additional agents. Additional agents useful in such co-administration include agents that improve the overall effectiveness of the effective dose of cells or decrease the dose of cells necessary to achieve an effect essentially equal to administration of an effective dose of the cells without the additional agent. Non-limiting examples of additional agents that may be co-administered with derived oogonia include: conventional agents for treating diseases of the infertility and the like.

By conventional agents for infertility is meant agents known in the art that prevent or inhibit infertility or dysfunction of the reproductive organs including but not limited to, e.g., gonadotropin-releasing hormone, oestrogen antagonists, gonadotropins and the like.

The cells may be introduced by injection, catheter, intravenous perfusion, surgery or the like. Cell may be used fresh or may be previously frozen. The cells may be frozen at liquid nitrogen temperatures and stored for long periods of time, being capable of use upon thawing. In some instances, the cells may be administered fresh such that the cells are collected and/or cultured and/or expanded and/or differentiated and administered without ever being frozen.

The cells (e.g., derived oogonia, ovarian progenitor cells, etc.) and/or compositions (e.g., derived oogonia and/or ovarian progenitor cell compositions) of this disclosure can be supplied in the form of a composition, comprising an isotonic excipient or buffer or media prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types.

In some instances, combined methods may be employed including e.g., where methods directed to in vivo expansion of oogonia are combined with other methods for increasing fertility, where methods directed to ex vivo expansion and transplantation of oogonia are combined with other methods for increasing fertility, where ex vivo and in vivo methods for oogonia expansion are combined, and the like. For example, in some instances, a subject may be administered an agent or a composition of agents for partial reprogramming of the ovary and subsequently administered a therapeutically effective dose of ex vivo expanded oogonia. In some instances, a subject may be administered a therapeutically effective dose of ex vivo expanded oogonia and subsequently administered an agent or a composition of agents for partial reprogramming of the ovary. In some instances, a subject may be concurrently administered an agent or a composition of agents for partial reprogramming of the ovary and a therapeutically effective dose of ex vivo expanded oogonia.

In some instances, administration of an amount of an agent or an amount of cells effective to enhance fertility of a subject may be combined with one or more additional therapies, including e.g., additional therapies directed at increasing the fertility of the subject. In some instances, a therapeutic regimen for enhancing the fertility of a subject may include administering platelet rich plasma to the subject.

The terms "co-administration" and "in combination with" include the administration of two or more therapeutic agents or therapeutic doses of cells or combinations thereof, either simultaneously, concurrently or sequentially within no specific time limits. In one embodiment, the agents and/or cells are present in a cell or in a subject's body at the same time or exert their biological or therapeutic effect at the same time. In one embodiment, the therapeutic agents are in the same composition or unit dosage form. In other embodiments, the therapeutic agents and/or cells are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As summarized above, the methods of the present disclosure include enhancing the fertility of a subject. Various subjects may be treated according to the subject methods. In some instances, the treated subject is a healthy subject, i.e., a subject not suffering from any chronic or acute affliction, condition or disease, including but not limited to e.g., cancer and the like. The fertility of healthy subjects may be enhanced, e.g., to the normal level of fertility of a corresponding but younger subject, including a subject 5 years younger, 10 years younger, 15 years younger, 20 years younger, 25 years younger, etc. In some instances, fertility of a subject may be enhanced to a level higher than that of a normal healthy individual of corresponding age.

Infertility, as used herein, is generally not considered a disease and, as such, a treated subject may be a healthy subject with infertility. Such subjects may be treated, e.g., to at least reduce the infertility in the subject and improve the subject's fertility, including where the subject's fertility is increased to that of a normally fertile subject of corresponding age (i.e., below average fertility may be increased to correspond with expected average fertility of a subject of corresponding age and health). In some instances, the fertility of a subject with below average fertility may be increased to a level above that of a normally fertile subject of corresponding age.

As summarized above, infertility may be the consequence of one or more adverse health conditions or disease. As such, in some instances, the methods may include treating an unhealthy subject (i.e., a subject with a disease or adverse health condition) with infertility that is a result of a disease or adverse health condition of the subject. Such subjects may be treated, e.g., to at least reduce the infertility in the subject and improve the subject's fertility, including where the subject's fertility is increased to that of a normally fertile subject of corresponding age (i.e., below average fertility may be increased to correspond with expected average fertility of a subject of corresponding age and health). In some instances, in the fertility of a subject with below average fertility may be increased to a level above that of a normally fertile subject of corresponding age.

The fertility of a subject may be determined or measured by any convenient means including e.g., the ability of the subject to conceive upon regular attempts (i.e., normally productive intercourse), the ovulation frequency of the subject, measuring the levels of one or more fertility related hormones or other fertility biomarkers, one or more imaging based diagnostic methods (including e.g., ultrasound imaging of the reproductive system including the ovaries), analysis and/or counting of one or more ovarian structures or cell types observed or retrieved from the ovary of the subject (e.g., as part of an in vitro fertilization (IVF) procedure or other infertility intervention).

In some cases, the fertility of the subject may be increased to prolong fertility in the subject, including healthy and unhealthy subjects. Fertility may be prolonged beyond the average of menopause, including where the average of menopause is adjusted or calculated for a particular subject, e.g., as based on demographic, life history, family history, or other factors. Accordingly, in some instances, fertility may be prolonged 1 year or more beyond the average age of menopause onset, including e.g., 2 years or more, 3 years or more, 4 years or more, 5 years or more, 10 years or more, etc. Where a subject is expected to have premature or early menopause onset (e.g., based on particular life history, family history, or one or more risk factors) the method may increase fertility in the subject closer to a normal level, including e.g., closer to the average age of menopause onset, including e.g., within 10 years or less of the average age of menopause onset, e.g., within 5 years or less, within 4 years or less, within 3 years or less, within 2 years or less, within 1 year or less, etc. In some instances, fertility of a subject at risk of premature or early menopause may be prolonged to at least an average age of menopause onset or beyond.

As summarized above, the present disclosure includes methods of treatment for enhancing fertility, restoring fertility of an infertile subject, enhancing the duration of fertility in a subject at risk of premature or early menopause, etc. Such methods may include administering an effective amount of an agent and/or cells to the subject. Effective amounts of the agents and/or cells are those administered amounts effective to enhance fertility, as described above, and/or amounts administered in order to prevent, ameliorate, inhibit the development of, or treat the fertility related symptoms of diseases or disorders related to or caused by infertility.

Treatment regimens, including the administration of agents and/or cells to a subject, of the present disclosure may vary. In some instances, the agent and/or cells may be administered chronically. In some instances, the agent and/or cells may be administered intermittently or for a predetermined duration or until a predetermined level of fertility is reached. Dosing of the agent may vary and may include e.g., semi-daily, daily, bi-daily, semi-weekly, weekly, bi-weekly, semi-monthly, monthly, bi-monthly, quarterly, semi-yearly, yearly, bi-yearly, etc.

As noted above, subjects treated according to the herein described methods may be treated chronically or for a finite time period. For example, the subject may be treated, e.g., administered an agent and/or cells, according to a predetermined treatment schedule, the length of which may vary and may range from multiple weeks or longer, including but not limited to e.g., 2 weeks or more, 3 weeks or more, a month or more, 2 months or more, 3 months or more, 4 months or more, 5 months or more, 6 months or more, 7 months or more, 8 months or more, 9 months or more, 10 months or more, 11 months or more, a year or more, 2 years or more, 3 years or more, 4 years or more, etc. A predetermined treatment course may include a dosing schedule, e.g., one or more dosing schedules described herein, including e.g., twice daily, daily, bi-daily, weekly, bi-weekly, monthly, bi-monthly, quarterly, twice a year, yearly, bi-yearly, and the like.

In some instances, a treatment schedule may include periodic dosing of an agent and/or cells to a subject, i.e., may include one or more "on" and "off" periods of dosing over the course of treatment. An "off" period of a doing schedule may be referred to as a holiday period. In a holiday period no agent and/or cells is delivered. A "holiday period", may vary, but in representative embodiments is at least about 1 day, such as at least about 2 days, including at least about 5 days, at least about 10 days, at least about 15 days, or longer. As such, embodiments of the methods include non-chronic (i.e., non-continuous) application of the agent and/or cells, e.g., non-chronic administration of an agent and/or cells for enhancing fertility.

A given course of treatment may include one or more holiday periods of the same or different length, including but not limited to e.g., one holiday period or more, two holiday periods or more, three holiday periods or more, four holiday periods or more, etc.

Particular treatment schedules may be generically applied to subjects broadly or specifically tailored or designed to the needs of individual subjects or groups of related subjects.

Analysis and Monitoring

As summarized above, in some instances, the methods of the present disclosure may include analyzing a subject and/or monitoring a subject, including e.g., where such analyzing and/or monitoring is employed as part of a therapeutic regimen to enhance fertility. A subject may be analyzed or monitored to assess the subject's fertility, including before, during (i.e., concurrent), or following (including immediate-, short- or long-term follow-up) treatment. The fertility of a subject may be determined or measured by any convenient means including e.g., the ability of the subject to conceive upon regular attempts (i.e., normally productive intercourse), the ovulation frequency of the subject, measuring the levels of one or more fertility related hormones or other fertility biomarkers, one or more imaging based diagnostic methods (including e.g., ultrasound imaging of the reproductive system including the ovaries), analysis and/or counting of one or more ovarian structures or cell types observed or retrieved from the ovary of the subject (e.g., as part of an in vitro fertilization (IVF) procedure or other infertility intervention).

The effectiveness of one or more agents and/or cells for enhancing fertility in a subject and monitoring of a subject who receives one or more of the subject agents can readily be determined by a person skilled in the medical and clinical arts. One or any combination of diagnostic methods, including physical examination, medical history and performance of analytical tests and methods described herein and practiced in the art (e.g., medical imaging including e.g., ultrasound) may be employed.

In some instances, monitoring may be employed to modulate a subject's therapy. For example, in some instances, an analysis of a subject may be performed (e.g., an analysis of a subject's fertility, an analysis of the presence of oogonia or ovarian progenitor cells in the subject, etc.) and the treatment of the subject may be altered based on the outcome of the assessment. Such monitoring may be performed continuously of discontinuously (i.e., intermittently). As such, the frequency of monitoring may vary and may include e.g., semi-daily, daily, bi-daily, semi-weekly, weekly, bi-weekly, semi-monthly, monthly, bi-monthly, quarterly, semi-yearly, yearly, bi-yearly, etc. In some instances, the result of an assessment directed to measuring fertility of a subject may indicate whether treatment should be initiated, altered, or terminated.

Monitoring and/or analysis may be performed on the subject (i.e., in vivo) or may be performed on a sample collected from the subject (i.e., ex vivo). In some instances, subjects may be monitored or analyzed for oogonia and/or ovarian progenitor cells, including the presence or amount of oogonia and/or ovarian progenitor cells in one or both ovaries of the subject. Such monitoring and/or analysis may be performed with or independent of treatment, including before, during (i.e., concurrent), or following (including immediate-, short- or long-term follow-up) treatment. In some instances, a subject may be assessed to determine if oogonia and/or ovarian progenitor cells are present in the subject's ovary. In some instances, a subject may be assessed to determine the amount of oogonia and/or ovarian progenitor cells present in the subject's ovary. In some instances, the result of an assessment directed to measuring or detecting oogonia and/or ovarian progenitor cells in the ovary may indicate whether treatment should be initiated, altered, or terminated.

Various means of assessing oogonia and/or ovarian progenitor cells may be employed, including e.g., detection of one or more oogonia and/or ovarian progenitor cells markers, e.g., as described above, or a cellular proliferation assessment. Useful cellular markers in assessing oogonia and/or ovarian progenitor cells include but are not limited to e.g., an oogonia linage marker, a pluripotency marker, a stem cell marker, a reprogramming marker, a marker of DNA double-strand breaks, a marker of DNA repair, a marker of tumor suppression, a marker of senescence, a marker of oxidative damage, an marker of epigenetic modification, a marker of proliferation and combinations thereof.

In some instances, assessments may include assessing the degree of partial reprogramming of cells of a subject. Any convenient method of assessing the degree of partial reprogramming of a cell may be employed including e.g., the expression of particular histone variants (e.g., gamma-H2AX downregulation), the expression of multipotency markers (e.g., Oct4), the expression of stress response genes (e.g., p16 down regulation, p21 downregulation, Atf3 downregulation, Gadd45b downregulation, etc.) the expression of senescence markers (e.g., MMP13 downregulation, etc.), monitoring epigenetic modifications (e.g., Histone H3 methylated Lys9 (H3K9), etc.), monitoring proliferation (phosphorylated histone H3 (H3P), Ki67, cyclins, etc.) and the like.

In some instances, cells may be subjected to analysis to provide early confirmation and identification of reprograming and/or partial reprogramming. In some instances, such analysis is conducted on an aliquot of cells (e.g., a sample or biopsy) by Southern blot, or other art-known methods which include, but are not limited, to MicroArray, NanoString, quantitative real time PCR (qPCR), whole genome sequencing, immunofluorescence microscopy, flow cytometry, and fluorescence activated cell sorting.

In some embodiments, detection of enzymatic activity of alkaline phosphatase, positive expression of the cell membrane surface markers SSEA3, SSEA4, Tra-1-60, Tra-1-81 and the expression of the KLF4, Oct3/4, Nanog, Sox2 transcription factors in, for example, presumptively reprogrammed human cells, may confirm reprogramming and/or indicate partial reprogramming of a cell.

In certain embodiments, marker detection and/or measurement of marker level is performed using flow cytometry. Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus. Fluorescence-activated cell sorting (FACS) is a specialized type of flow cytometry. FACS provides a method for sorting a heterogeneous mixture of biological cells into two or more containers, generally one cell at a time, based upon the specific light scattering and fluorescent characteristics of each cell. The flow cytometer and the FACS machine are useful scientific instruments as they provide fast, objective and quantitative recording of signals, e.g., fluorescent signals, and/or detection of cellular characteristics, e.g., size, granularity, viability, etc., from individual cells as well as physical separation of cells of particular interest. Fluorescent signals used in flow cytometry, for instance when quantifying and/or sorting cells by any marker present on or in the cell, typically are fluorescently-tagged antibody preparations or fluorescently-tagged ligands for binding to antibodies or other antigen-, epitope- or ligand-specific agent, such as with biotin/avidin binding systems or fluorescently-labeled and optionally addressable beads (e.g. microspheres or microbeads). The markers or combinations of markers detected by the optics and/or electronics of a flow cytometer vary and in some cases include but are not limited to: cell surface markers, intracellular and nuclear antigens, DNA, RNA, cell pigments, cell metabolites, protein modifications, transgenic proteins, enzymatic activity, apoptosis indicators, cell viability, cell oxidative state, etc.

In certain instances, flow cytometry is performed using a detection reagent, e.g., a fluorochrome-labeled antibody, e.g., a monoclonal antibody, with specific avidity against a cell surface maker of interest. A cellular sample is contacted with a detection reagent under conditions sufficient to allow the detection reagent to bind the cell surface maker and the cells of the sample are loaded into the flow cytometer, e.g., by first harvesting the cells from a cell culture using methods known in the art or described herein and re-suspending the isolated cells in a suitable buffer, e.g., running buffer. The cells loaded into the flow cytometer are run through the flow cytometer, e.g., by flowing cell containing buffer or liquid sample through the flow cell of the flow cytometer. The flow cytometer detects events as the cell passes one or more detection areas of the flow cytometer. For example, the flow cytometer may detect fluorescence emitted from a fluorochrome of a detection reagent upon excitation of the fluorochrome with a particular wavelength of light. In some instances, the flow cytometer detects the relative intensity of a particular signal, e.g., fluorescence of a particular detection reagent, of a particular cell, e.g., to quantify the level of a marker present on the surface of the cell and/or to qualitatively categorize the cell, e.g., as a cell that is positive for a particular marker or a cell that is negative for a particular marker. Detected events are counted or otherwise evaluated by the flow cytometer with or without input from an operator and used to determine, e.g., the total number of cells, the number or proportion of cells bound to a particular detection reagent, etc. In instances where FACS is utilized cells may be sorted, e.g., into separate containers, based on the detection or measurement of a particular marker. In some instances, cell sorting, e.g., by FACS, may be utilized to generate a purified population of a desired cell type.

In some instances, a threshold level of a particular detectable marker is used to categorize cells for sorting by FACS. Threshold levels may be used to categorize cells as "positive", "negative, "high", "low", etc. for a particular marker based on the level of detection of the marker. In some instances, a marker threshold level is determined by making a comparison of the levels of marker within a population of cells, e.g., a population of cells of unknown expression levels of Marker X or a population of cells suspected of containing subpopulations of cells having different expression levels of Marker X. For example, the expression level of Marker X is measured on a flow cytometer of at least a sufficient number of cells such that the measurements may be plotted, e.g., on a histogram, and separation between two or more subpopulations of cells is revealed based on individual cell expression levels of Marker X. Accordingly, the flow cytometer operator may then determine a threshold level between the subpopulations that may be used to categorize cells as belonging to a particular subpopulation, e.g., a subpopulation having a low level of expression of Marker X or a subpopulation having high level of expression of Marker X.

Expression markers of interest may be used to identify a particular cell type or verify that a derived cell type expresses a characteristic component of the derived cell type. In some instances, detection of expression markers may allow for optimization of a particular differentiation protocol, e.g., to optimize production of a desired cell type based on detection of one or more expression markers. Expression markers will vary depending on the type of cell to be identified or verified and/or desired downstream uses of the cell following identification or verification with the expression marker. Types of expression markers will include but are not limited to, e.g., gene expression marker, protein expression markers, expressed reporters, and the like. Expression marker detection and/or measurement may be detrimental to cell viability (e.g., wherein detection requires lysing or fixing a cell of interest) or may be essentially neutral to cell viability (e.g., wherein detection does not require lysing or fixing a cell of interest and may be performed on live cells).

Gene expression markers include but are not limited to the presence, absence, and/or relative amounts of a particular gene transcript that is indicative of particular cell type. Protein expression markers include but are not limited to the presence, absence, and/or relative amounts of a particular expression product that is indicative of particular cell type. Protein expression markers may be intercellular proteins, intracellular proteins or cell surface proteins. In some instances, a gene expression marker and a protein expression marker derived from the same gene may be indicative of a particular cell type.

Methods of detecting and/or measuring gene expression and/or protein expression are well-known in the art and include but are not limited to, e.g., Northern blot, Western blot, ELISA, PCR, quantitative PCR, in situ hybridization, fluorescent in situ hybridization, immunohistochemistry, immunofluorescence, microarray, quantitative sequencing, RNAseq, quantitative mass spectrometry, and the like.

Flow cytometric analysis methods may be employed at any convenient point in the subject methods, including e.g., analysis and/or sorting of cells to be isolated for ex vivo expansion, analysis and/or sorting of cells to be evaluated for in vivo reprogramming (including partial and/or complete), monitoring of the effectiveness of an ongoing treatment regimen, counting and/or other analysis of cells obtained from a treated subject (e.g., in order to evaluate oogonia or ovarian progenitor cells obtained from the treated subject), and the like.

The assessments and monitoring described herein may be combined with regular health assessments of a subject, including e.g., regular check-ups or diagnostic procedures, such as e.g., regular gynecological procedures. In some instances, the assessments and monitoring described herein may be performed independently from any regular health assessment of the subject.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of enhancing the fertility of a female subject by in vivo expansion of oogonia, the method comprising increasing the number of oogonia present in the ovary of the female subject by locally introducing nucleic acids encoding a combination of-reprogramming factors to the ovary cells of the female subject in vivo via a vector, wherein the combination of reprogramming factors comprises Oct4, Sox2, Klf4, and c-Myc.

2. The method according to claim 1, wherein the ovary cells of the female subject comprise ovarian stem cells.

3. The method according to claim 1, wherein the method comprises subjecting the ovary cells of the female subject to the combination of reprogramming factors for a period of less than 2 weeks.

4. The method according to claim 3, wherein the period of less than 2 weeks is followed by a holiday period.

5. The method according to claim 3, wherein the method comprises 2 or more periods of subjecting the ovary cells of the female subject to the combination of reprogramming factors.

6. The method according to claim 1, wherein the method comprises subjecting the ovary cells of the female subject to the combination of reprogramming factors cyclically.

7. The method according to claim 1, wherein female subject is postmenopausal.

8. The method according to claim 1, wherein the vector is a viral vector.

9. The method according to claim 8, wherein the viral vector is chosen from a retrovirus, a lentivirus, an adenovirus, an adeno associated virus, a herpes virus, a Sindbis virus, a pox virus, a baculovirus, a bacterial phage, and a Sendai virus.

10. The method according to claim 1, wherein the vector is engineered to target an ovarian cell type by binding to an ovary lineage marker expressed on the surface of the targeted cell.

11. The method according to claim 10, wherein the binding to an ovary lineage marker is mediated by a targeting ligand displayed on the vector particle surface, wherein the targeting ligand comprises a single-chain antibody.

12. The method according to claim 11, wherein the ovary lineage marker is chosen from lymphocyte antigen 6 complex, locus A (LY6A); Lgr5; FOXL2; NR2F2; VASA; and NANOS.

13. The method according to claim 1, wherein the combination of reprogramming factors further comprises a reprogramming factor selected from Lin28, Nanog, hTert and SV40 large T antigen.

* * * * *